United States Patent
Matsui et al.

(10) Patent No.: US 7,834,238 B2
(45) Date of Patent: Nov. 16, 2010

(54) SASPASE KNOCKOUT ANIMAL

(75) Inventors: Takeshi Matsui, Bunkyo-ku (JP); Fumie Kisumi, Kobe (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 69 days.

(21) Appl. No.: 12/088,640

(22) PCT Filed: Oct. 4, 2006

(86) PCT No.: PCT/JP2006/319834

§ 371 (c)(1),
(2), (4) Date: Jun. 18, 2008

(87) PCT Pub. No.: WO2007/043404

PCT Pub. Date: Apr. 19, 2007

(65) Prior Publication Data

US 2010/0005534 A1     Jan. 7, 2010

(30) Foreign Application Priority Data

Oct. 11, 2005   (JP) ............................. 2005-296611

(51) Int. Cl.
*A16K 15/00*   (2006.01)
(52) U.S. Cl. ............................. 800/18; 800/3
(58) Field of Classification Search ............ 800/3, 800/8, 18
See application file for complete search history.

(56) References Cited

FOREIGN PATENT DOCUMENTS

JP    2006-511204 A    4/2006

WO    WO 03/078458 A2    9/2003

OTHER PUBLICATIONS

Wagner (May 1995, Clin. and Experimental Hypertension, vol. 17, pp. 593-605).*
Mullins (1996, J. Clin. Invest., vol. 98, 1557-1560).*
. Wall (1996, Theriogenology, vol. 45, p. 57-68).*
Ebert (1988, Mol. Endocrinology, vol. 2, pp. 277-283).*
Mullins (1990, Nature, vol. 344, p. 541-544).*
Hammer (1990, Cell, vol. 63, p. 1099-1112).*
Mullins, 1989, EMBO, vol. 8, p. 4065-4072.*
Taurog, 1988, J. Immunol., vol. 141, p. 4020-4023.*
Matsui (J. Biol. Chem, Sep. 15, 2006, vol. 281, No. 37, p. 27512-27525).*
Bernard, D., et al., "Identification and characterization of a novel retroviral-like aspartic protease specifically expressed in human epidermis," *J. Invest. Dermatol.*, vol. 125(2), pp. 278-287 (Aug. 2005).
Egberts, F., et al., "Cathepsin D is involved in the regulation of transglutaminase 1 and epidermal differentiation," *Journal of Cell Science*, vol. 117(Pt 11), pp. 2295-2307 (May 1, 2004).

* cited by examiner

*Primary Examiner*—Michael C. Wilson
(74) *Attorney, Agent, or Firm*—Townsend and Townsend and Crew LLP

(57) ABSTRACT

Knockout animals in which a gene encoding a SASPase has been deleted (hereinafter, referred to as SASPase KO animals) are provided. The SASPase KO animals deficient in expression of functional SASPase were produced by deleting a gene encoding a stratified epithelium-specific protease, SASPase, through targeted disruption. The SASPase KO animals showed a significant increase in wrinkles on the sides of the body and so on. The SASPase KO animals find utility as animal models of wrinkles.

3 Claims, 4 Drawing Sheets

A  +/-    -/-

B  +/-  -/-

SEQUENCE LISTING

```
<160> NUMBER OF SEQ ID NOS: 5

<210> SEQ ID NO 1
<211> LENGTH: 1556
<212> TYPE: DNA
<213> ORGANISM: Mus musculus
<220> FEATURE:
<221> NAME/KEY: CDS
<222> LOCATION: (7)..(1023)

<400> SEQUENCE: 1 aggaga atg agg aac cct ggg ggc cca ggt tgg gca tca aaa agg ccc         48
       Met Arg Asn Pro Gly Gly Pro Gly Trp Ala Ser Lys Arg Pro
       1               5                   10 ctg cag aag aag cag aac aca gcc tgc ctc tgt gcc cag cag cca gcc         96
Leu Gln Lys Lys Gln Asn Thr Ala Cys Leu Cys Ala Gln Gln Pro Ala
15                  20                  25                  30 aga cac ttt gta ccg gct ccc ttc aac tcg tcc agg cag ggc aag aac        144
Arg His Phe Val Pro Ala Pro Phe Asn Ser Ser Arg Gln Gly Lys Asn
                35                  40                  45 acg gcc cag ccg aca gag ccc tcg ctc tcc agc gtg att gcg ccc aca        192
Thr Ala Gln Pro Thr Glu Pro Ser Leu Ser Ser Val Ile Ala Pro Thr
            50                  55                  60
```

```
ctc ttc tgt gcg ttt ctt tac ttg gct tgt gtt act gct gaa ctt cca        240
Leu Phe Cys Ala Phe Leu Tyr Leu Ala Cys Val Thr Ala Glu Leu Pro
         65                  70                  75 gag gtg agc aga agg atg gcc acc agc gga gtc aga agc aag gaa gga        288
Glu Val Ser Arg Arg Met Ala Thr Ser Gly Val Arg Ser Lys Glu Gly
     80                  85                  90 cgc cgg gag cat gcc ttc gtc cca gaa cct ttc act ggt act aac tta        336
Arg Arg Glu His Ala Phe Val Pro Glu Pro Phe Thr Gly Thr Asn Leu
 95                 100                 105                 110 gct ccc agc ctt tgg ctg cac cgc ttt gaa gtc att gat gac ctc aac        384
Ala Pro Ser Leu Trp Leu His Arg Phe Glu Val Ile Asp Asp Leu Asn
                115                 120                 125 cat tgg gat cat gcc acc aaa ctg agg ttc ctg aaa gag tcg ctc aag        432
His Trp Asp His Ala Thr Lys Leu Arg Phe Leu Lys Glu Ser Leu Lys
            130                 135                 140 gga gat gcc ctg gat gtc tac aat gga ctc agt tcc cag gcc cag ggc        480
Gly Asp Ala Leu Asp Val Tyr Asn Gly Leu Ser Ser Gln Ala Gln Gly
145                 150                 155 gat ttc agt ttt gtg aag caa gcc ctc ctg agg gcc ttt ggg gcc cct        528
Asp Phe Ser Phe Val Lys Gln Ala Leu Leu Arg Ala Phe Gly Ala Pro
    160                 165                 170 ggg gag gcc ttc agt gag ccc gaa gag att ttg ttt gcc aac agc atg        576
Gly Glu Ala Phe Ser Glu Pro Glu Glu Ile Leu Phe Ala Asn Ser Met
175                 180                 185                 190 ggt aag ggc tac tac ctt aaa ggg aag gtt ggc cat gtg cct gtg aga        624
Gly Lys Gly Tyr Tyr Leu Lys Gly Lys Val Gly His Val Pro Val Arg
                195                 200                 205 ttc ctg gtg gac tct ggg gct cag gtg tct gtg gtt cac ccc gcc tta        672
Phe Leu Val Asp Ser Gly Ala Gln Val Ser Val Val His Pro Ala Leu
            210                 215                 220 tgg gag gag gtc act gat ggt gac ctg gat act ctt cgt cct ttt aac        720
Trp Glu Glu Val Thr Asp Gly Asp Leu Asp Thr Leu Arg Pro Phe Asn
                225                 230                 235 aat gtg gtc aaa gtg gcc aat ggg gca gag atg aag atc ttg ggt gtg        768
Asn Val Val Lys Val Ala Asn Gly Ala Glu Met Lys Ile Leu Gly Val
240                 245                 250 tgg gac aca gaa att agc ctg ggc aag aca aag ctg aag gcc gag ttt        816
Trp Asp Thr Glu Ile Ser Leu Gly Lys Thr Lys Leu Lys Ala Glu Phe
255                 260                 265                 270 ctg gtg gcc aac gcc agc gca gaa gag gct att att ggc aca gac gtc        864
Leu Val Ala Asn Ala Ser Ala Glu Glu Ala Ile Ile Gly Thr Asp Val
                275                 280                 285 ttg cag gac cac aat gcc gtg ctg gac ttc gaa cac cgc acc tgc acc        912
Leu Gln Asp His Asn Ala Val Leu Asp Phe Glu His Arg Thr Cys Thr
            290                 295                 300 ctg aag ggg aag aag ttc cgc ctg ctc cct gtc ggg agc tcc ttg gag        960
Leu Lys Gly Lys Lys Phe Arg Leu Leu Pro Val Gly Ser Ser Leu Glu
305                 310                 315 gat gag ttt gac ctg gag ctt att gag gaa gag ggg tct tct gca           1008
Asp Glu Phe Asp Leu Glu Leu Ile Glu Glu Glu Gly Ser Ser Ala
            320                 325                 330 ccg gag ggc tcc cac taagaaaccc catttcttgt tcccagcatt ggtagggga        1063
Pro Glu Gly Ser His
335 ctttgtgttg gggggagcag atgtcctggg gggtatcatc cggcctagcc agtctttaca    1123 ccggttctca gtttccctcc ttctacaggg gccttgcttt gcctttgttt ggggagggag    1183 gccagcttgg tggcctaaag cagtgtcccc aaggtctgca aagacttcca aggctggcag    1243 gagcttctga ggaagccagg aatgtcaatc ttgagagagg acccttttag atcccctgaa    1303
```

-continued

```
gtatggctca gtcactttca cgtccccaag cctgctgagc tgagcctggt cttggctaag      1363
accctcacaa tccagatgct tggaggagac tggcagctgc tctgggagtc ctccctgagt      1423
cctcccacct gcacaaggat gctccctcct gtcctgtcac ttgccttgaa tctcatggag      1483
cctgtatcaa taattcaatt atttcaaaac accaataaag atctgttcat ggaaaaaaaa      1543
aaaaaaaaaa aaa                                                         1556
```

<210> SEQ ID NO 2
<211> LENGTH: 339
<212> TYPE: PRT
<213> ORGANISM: Mus musculus

<400> SEQUENCE: 2

```
Met Arg Asn Pro Gly Gly Pro Gly Trp Ala Ser Lys Arg Pro Leu Gln
1               5                   10                  15

Lys Lys Gln Asn Thr Ala Cys Leu Cys Ala Gln Gln Pro Ala Arg His
                20                  25                  30

Phe Val Pro Ala Pro Phe Asn Ser Ser Arg Gln Gly Lys Asn Thr Ala
            35                  40                  45

Gln Pro Thr Glu Pro Ser Leu Ser Ser Val Ile Ala Pro Thr Leu Phe
        50                  55                  60

Cys Ala Phe Leu Tyr Leu Ala Cys Val Thr Ala Glu Leu Pro Glu Val
65                  70                  75                  80

Ser Arg Arg Met Ala Thr Ser Gly Val Arg Ser Lys Glu Gly Arg Arg
                85                  90                  95

Glu His Ala Phe Val Pro Glu Pro Phe Thr Gly Thr Asn Leu Ala Pro
            100                 105                 110

Ser Leu Trp Leu His Arg Phe Glu Val Ile Asp Asp Leu Asn His Trp
        115                 120                 125

Asp His Ala Thr Lys Leu Arg Phe Leu Lys Glu Ser Leu Lys Gly Asp
    130                 135                 140

Ala Leu Asp Val Tyr Asn Gly Leu Ser Ser Gln Ala Gln Gly Asp Phe
145                 150                 155                 160

Ser Phe Val Lys Gln Ala Leu Leu Arg Ala Phe Gly Ala Pro Gly Glu
                165                 170                 175

Ala Phe Ser Glu Pro Glu Ile Leu Phe Ala Asn Ser Met Gly Lys
            180                 185                 190

Gly Tyr Tyr Leu Lys Gly Lys Val Gly His Val Pro Val Arg Phe Leu
        195                 200                 205

Val Asp Ser Gly Ala Gln Val Ser Val Val His Pro Ala Leu Trp Glu
    210                 215                 220

Glu Val Thr Asp Gly Asp Leu Asp Thr Leu Arg Pro Phe Asn Asn Val
225                 230                 235                 240

Val Lys Val Ala Asn Gly Ala Glu Met Lys Ile Leu Gly Val Trp Asp
                245                 250                 255

Thr Glu Ile Ser Leu Gly Lys Thr Lys Leu Lys Ala Glu Phe Leu Val
            260                 265                 270

Ala Asn Ala Ser Ala Glu Glu Ala Ile Ile Gly Thr Asp Val Leu Gln
        275                 280                 285

Asp His Asn Ala Val Leu Asp Phe Glu His Arg Thr Cys Thr Leu Lys
    290                 295                 300

Gly Lys Lys Phe Arg Leu Leu Pro Val Gly Ser Ser Leu Glu Asp Glu
305                 310                 315                 320
```

```
Phe Asp Leu Glu Leu Ile Glu Glu Glu Gly Ser Ser Ala Pro Glu
            325                 330                 335

Gly Ser His

<210> SEQ ID NO 3
<211> LENGTH: 26
<212> TYPE: DNA
<213> ORGANISM: Artificial
<220> FEATURE:
<223> OTHER INFORMATION: an artificially synthesized sequence

<400> SEQUENCE: 3
ccaagttcta attccatcag aagctg                                              26

<210> SEQ ID NO 4
<211> LENGTH: 29
<212> TYPE: DNA
<213> ORGANISM: Artificial
<220> FEATURE:
<223> OTHER INFORMATION: an artificially synthesized sequence

<400> SEQUENCE: 4
agcttgagcc cttgagccca cagatttac                                           29

<210> SEQ ID NO 5
<211> LENGTH: 30
<212> TYPE: DNA
<213> ORGANISM: Artificial
<220> FEATURE:
<223> OTHER INFORMATION: an artificially synthesized sequence

<400> SEQUENCE: 5
actatctatc tagctatctg catgtctatc                                          30
```

SASPASE KNOCKOUT ANIMAL

CROSS-REFERENCES TO RELATED APPLICATIONS

This application is a U.S. National Stage Application of PCT/JP2006/319834, filed Oct. 4, 2006, which claims the benefit of Japanese Application No. 2005-296611, filed Oct. 11, 2005.

TECHNICAL FIELD

The present invention relates to non-human animals deficient in a stratified epithelium-specific protease, SASPase.

BACKGROUND ART

SASPase is a protease found in human skin that has a molecular weight of 28 kDa. SASPase is specifically expressed in the granular layer of human skin, and produces a 14 kDa protein by an autolysis (Bernard D. et al., J. Invest. Dermatol. 125, 278-287, 2005).

Recombinant SASPase has been reported to demonstrate autolytic activity as well as to degrade exogenous substrates such as insulin and casein (Bernard D. et al., J. Invest. Dermatol. 125, 278-287, 2005). However, its function in the epidermis has yet to be determined. [Non-Patent Document 1] Bernard D. et al., J. Invest. Dermatol. 125, 278-287, 2005

DISCLOSURE OF THE INVENTION

Problem to be Solved by the Invention

An objective of the present invention is to provide knockout animals deficient in a gene encoding SASPase or a gene homologous to the gene (hereinafter referred to as SASPase KO animals).

Means for Solving the Problems

The present inventors aimed to produce SASPase KO mice in which a gene encoding SASPase was deleted though targeted disruption.

As a result, from the age of about 5 weeks, the sides of the body of the SASPase KO mice were observed to possess numerous wrinkles in parallel. Accordingly, the SASPase KO mice were suggested to be useful as a model for analyzing wrinkles attributable to the epidermis, thereby leading to completion of the present invention.

That is, the present invention relates to non-human animals deficient in functional SASPase in which a gene encoding SASPase or a gene homologous to the gene has been deleted, preferably by targeted disruption. The non-human animals are preferably rodents, and more preferably mice.

As used herein, the term "targeted disruption" refers to a technique for introducing a mutation into a target gene that involves introducing into cells a DNA in which a mutation has been introduced into the nucleotide sequence of the target gene, preferably a DNA into which a selection marker has been inserted, and more preferably a DNA into which a drug resistance gene has been inserted; and selecting cells in which homologous recombination has occurred between the introduced DNA and the target gene (Suzanne, L. et al., Nature 336, 348, 1988). More specifically, when a gene encoding SASPase is deleted by targeted disruption, whole or a portion of the gene is replaced with an exogenous nucleic acid used for targeted disruption. The exogenous nucleic acid may simply be a sequence derived from a genome from which a gene encoding SASPase has been deleted, or may contain a desired sequence. For example, the nucleic acid may contain a desired marker gene, preferably a drug resistance gene. Targeted disruption is an example of a technique for deleting a gene encoding SASPase based on its nucleotide sequence information; however, any technique for deleting the gene based on its nucleotide sequence information may be utilized in the context of the present invention. In addition, the phrase "deleting a gene" refers to introducing a mutation into a gene and thereby causing loss of function of a gene product.

Furthermore, the term "functional SASPase" refers to SASPase that retains its protease activity. Deficiency in functional SASPase can be confirmed by the substantial absence of SASPase which may be observed in the granular layer of the epidermis by immunostaining and the like. "Substantial absence" refers to preferably 1/5 or less, more preferably 1/10 or less, even more preferably 1/20 or less of the amount of SASPase detected in the wild-type granular layer of the epidermis, and even more preferably to an amount that is below the detection limit (or background level).

In the course of the present invention, it was discovered that mice deficient in functional SASPase developed and grew to demonstrate an abnormality accompanying the deficiency in SASPase in which wrinkles are formed on the sides of the body, and that such mice are useful for analyzing the function of SASPase in living organisms.

A nucleotide sequence of a genomic DNA containing the SASPase gene isolated by the present inventors is designated herein as SEQ ID NO: 1, and the amino acid sequence of the protein encoded by the DNA is designated herein as SEQ ID NO: 2. The polypeptide translated from the codon at positions 256 to 258 that encodes the second methionine in SEQ ID NO: 1 (polypeptide containing the amino acid sequence from positions 84 to 339 of SEQ ID NO: 2), produces an active fragment having protease activity (polypeptide containing the amino acid sequence from positions 189 to 324 of SEQ ID NO: 2) by auto-processing. Although a gene encoding SASPase may have polymorphisms within a species and differences arising between species, the region corresponding to the amino acid sequence from positions 84 to 339 of SEQ ID NO: 2, particularly the region of an active fragment corresponding to the amino acid sequence from positions 189 to 324 of SEQ ID NO: 2, is highly conserved.

In the context of the present invention, the phrase "a gene encoding SASPase or a gene homologous to the gene" refers to a gene encoding a polypeptide containing the amino acid sequence of SEQ ID NO: 2, a polymorphic gene of the gene in the same species, and a gene encoding a peptide having the same protease activity as the polypeptide that is conserved across species.

A DNA which is highly homologous to the nucleotide sequence of SEQ ID NO: 1 and that contains a nucleotide sequence encoding a protease is considered "a gene encoding SASPase or a gene homologous to the gene". A DNA encoding a polypeptide that contains an amino acid sequence highly identical to the amino acid sequence of SEQ ID NO: 2, and in particular contains an amino acid sequence highly identical to the active center of the protease activity and/or the processing site is also considered "a gene encoding SASPase or a gene homologous to the gene". For example, the term "SASPase" as used in context of the present invention encompasses a polypeptide containing an amino acid sequence highly identical to the amino acid sequence from positions 189 to 324 of SEQ ID NO: 2 that encodes a fragment having protease activity, and more preferably a polypeptide containing an amino acid sequence highly identical to the amino acid sequence from positions 84 to 339 of SEQ ID NO: 2. Specifically, a gene encoding SASPase in the present invention includes a gene containing a DNA of the following (i) or (ii):

(i) a DNA encoding a polypeptide containing the amino acid sequence from positions 84 to 339 of SEQ ID NO: 2, or a polypeptide containing the amino acid sequence from positions 189 to 324;

(ii) a DNA encoding a polypeptide containing the amino acid sequence from positions 84 to 339 of SEQ ID NO: 2, or a polypeptide which is highly identical to the amino acid sequence from positions 189 to 324 and has protease activity.

As used herein, the term "highly identical" refers to sequence identity of, for example, 70% or more, preferably 80% or more, 85% or more, 90% or more, and most preferably 95% or more (for example, 96%, 97%, 98%, or 99% or more). The identity of an amino acid sequence or nucleotide sequence can be calculated by aligning sequences to be compared by appropriately inserting gaps so that the amino acids or nucleotides are matched, and by determining the percentage (%) of matched amino acids or nucleotides in all amino acids or nucleotides within the aligned range. Sequence alignment can be carried out by using, for example, the BLAST algorithm developed by Karlin and Altschul (Proc. Natl. Acad. Sci. USA, 1990, 87, 2264-2268; Karlin, S. & Altschul, S. F., Proc. Natl. Acad. Sci. USA, 1993, 90, 5873). Programs called BLASTN and BLASTP have been developed based on the BLAST algorithm (Altschul, S. F. et al., J. Mol. Biol. 1990, 215, 403). When a nucleotide sequence is analyzed using BLASTN, parameters are set to, for example, score=100 and wordlength=12. In addition, when analyzing an amino acid sequence using BLASTP, parameters are set to, for example, score=50 and wordlength=3. When using the BLAST or Gapped BLAST programs, the default parameters of each program are used. Specific procedures for these analytical methods are known (see the BLAST web site in the National Center for Biotechnology Information (NCBI)). When determining the identity of a sequence, the percentage of matched nucleotides in alignment can be calculated by considering gaps as mismatches. In the context of the present invention, a gene encoding SASPase includes a naturally-occurring DNA which encodes a protease containing an amino acid sequence that is highly identical to an amino acid sequence of an active fragment having protease activity (for example, positions 189 to 324 of SEQ ID NO: 2) of a polypeptide containing the amino acid sequence of SEQ ID NO: 2.

As used herein, "a gene encoding SASPase" also includes a gene that can hybridize with a targeting vector produced based on the nucleotide sequence information described in SEQ ID NO: 1 and undergo homologous recombination, and can be deleted through targeted disruption. More specifically, "a gene encoding SASPase" includes a gene containing a DNA of the following (a) or (b):

(a) a DNA containing the nucleotide sequence of SEQ ID NO: 1 or its coding sequence;

(b) a DNA encoding a protease that hybridizes under stringent conditions with a DNA containing the nucleotide sequence of SEQ ID NO: 1 or its coding sequence, or complementary strands thereof.

In addition, "a gene encoding SASPase" includes a gene containing a DNA of the following (c) or (d):

(c) a DNA containing a nucleotide sequence from positions 256 to 1023 or from positions 571 to 978 of SEQ ID NO: 1;

(d) a DNA encoding a protease that hybridizes under stringent conditions with the DNA of (c) or a complementary strand thereof.

For example, a gene encoding SASPase in the present invention includes a DNA which encodes a protease and to which a probe prepared from a DNA containing the nucleotide sequence of SEQ ID NO: 1 (for example, positions 1 to 1535), preferably the nucleotide sequence from positions 256 to 1023 of SEQ ID NO: 1, and more preferably the nucleotide sequence from positions 571 to 978 of SEQ ID NO: 1, or a DNA containing a complementary sequence thereof, hybridizes under stringent conditions. Probes can be prepared using, for example, the random primer method (Feinberg, A. P. and Vogelstein, B., Anal. Biochem. 132, 6-13, 1983; Feinberg, A. P. and Vogelstein, B., Anal. Biochem. 137, 266-267, 1984) (by using, for example, the Random Primer DNA Labeling Kit, Takara Bio Inc., Otsu, Japan). A "protease" refers to a polypeptide having proteolytic activity (also referred to as protease activity). Protease activity can be determined by fluorometry, for example, by measuring proteolytic activity on a fluorescent-labeled substrate using the Enzchek™ Protease Assay Kit (Molecular probe). Although insulin or casein or the like can be used for a substrate, the present invention is not particularly limited thereto. In the context of the present invention, an example of stringent conditions includes hybridization in 4×SSC at 65° C. (1×SSC contains 150 mM NaCl and 15 mM sodium citrate), 7% (W/V) sodium dodecyl sulfate (SDS), 100 µg/ml denatured salmon sperm DNA, and 5×Denhardt's solution (1×Denhardt's solution contains 0.2% polyvinyl pyrrolidone, 0.2% bovine serum albumin, and 0.2% Ficoll), followed by washing in 0.5×SSC for 1 hour at 60° C. A more preferred washing condition is the washing in 0.1×SSC for 1 hour at 65° C. An alternate example of stringent conditions includes hybridization in 4×SSC containing 50% formamide at 42° C. Washing may be carried out under the same conditions as described above. For example, a naturally-occurring DNA encoding SASPase can be isolated by screening a desired mammalian cDNA library or genomic library. Examples of genes encoding SASPase include Accession No. XM_575593 (protein ID: XP_575593), Accession No. XM_580888 (protein ID: XP_580888), and Accession No. XM_538536 (protein ID: XP_538536).

The present invention also relates to methods for increasing wrinkles and/or sags, such methods including the step of deleting a gene encoding SASPase or gene homologous to the gene. Since animals deficient in the gene demonstrate increased wrinkles and/or sags, they are useful for analyzing the mechanism of wrinkles and/or sags, and for performing treatments or assaying pharmaceutical agents to prevent or reduce wrinkles and/or sags.

Furthermore, the present invention relates to methods for analyzing the functions of SASPase by comparing an animal deficient in a gene encoding SASPase or gene homologous to the gene, with a wild-type animal, and then analyzing the phenotype of the animal deficient in a gene encoding SASPase. The above-mentioned "functions" contains the role played by SASPase after birth or in an adult as well as the role played during ontogenesis.

In addition, the present invention relates to methods for using animals deficient in a gene encoding SASPase as animal models of diseases caused by SASPase deficiency to analyze these diseases.

The present invention also provides methods for using animals deficient in a gene encoding SASPase as animal models of wrinkles, such methods including the step of measuring wrinkles. Measurements of wrinkles includes desired measurements relating to wrinkles, such as measurements of the presence or absence of wrinkles, the time of appearance of wrinkles, and the degree of wrinkles. Measurement of the degree of wrinkles encompasses any desired qualitative, quantitative or semi-quantitative wrinkle measurements in which the degree can be compared, such as measurements including the number, density, depth, and length of wrinkles, the degree of sags, and flexibility. Specific examples of wrinkle measurement methods include analytical evaluation of wrinkle images with oblique illumination, analytical evaluation by semitransparent replica transmission, and analytical evaluation using a three-dimensional coordinate measurement system (Guidance for Wrinkle Evaluation by the Japan Cosmetic Industry Association, Journal of Japanese Cosmetic Science Society, Vol. 28, No. 2, p. 118-128, 2004).

Accordingly, the present invention relates to animals in which a gene encoding SASPase has been knocked out and uses thereof. More specifically, the present invention relates to the following:

[1] a non-human animal deficient in functional SASPase, in which a gene encoding SASPase or a homologous gene thereof has been deleted;

[2] the non-human animal of [1], wherein the gene encoding SASPase or homologous gene thereof has been deleted through targeted disruption;

[3] the non-human animal of [1] or [2], wherein the animal is a rodent;

[4] the non-human animal of [3], wherein the rodent is a mouse;

[5] the non-human animal of any of [1] to [4], wherein the deleted gene comprises the DNA of the following (a) or (b):
    (a) a DNA comprising the nucleotide sequence of SEQ ID NO: 1 or the coding sequence thereof, or
    (b) a DNA encoding a protease that hybridizes under stringent conditions with a DNA comprising the nucleotide sequence of SEQ ID NO: 1 or the coding sequence thereof; and

[6] a method for using the non-human animal of any of [1] to [5] as an animal model of a wrinkle, wherein the method comprises the step of measuring a wrinkle.

MODES FOR CARRYING OUT THE INVENTION

Figure 1:
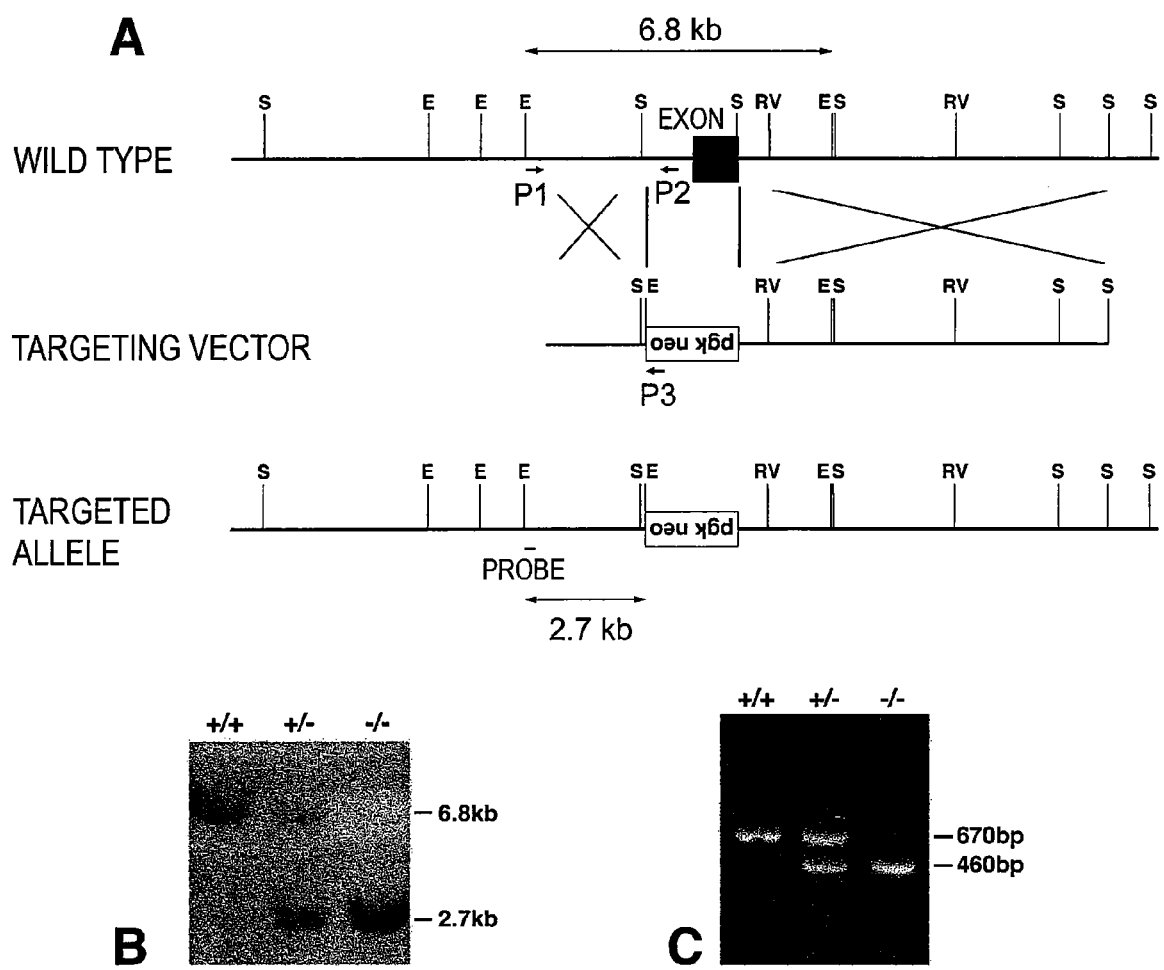
FIG. 1 demonstrates the method utilized to produce the SASPase KO mouse. Part A is composed of a diagram depicting the structure of a targeting vector, in which the region of a probe used in Southern blotting is indicated. PCR primers for genotyping are indicated as P1, P2, and P3. Part B depicts the results of Southern blotting. Mouse genomic DNAs digested with the enzyme EcoRI were analyzed by Southern blotting using a probe outside of the 5'-side homologous recombination region. A 6.8 kb band and a 2.7 kb band were detected in wild-type mice and the knockout mice, respectively. Part C depicts the results of genomic PCR. Genomic PCR was carried out using mouse genomic DNAs. A 670 bp product and a 460 bp product were detected in wild-type mice and the knockout mice, respectively.

Herein below, embodiments of the present invention are described in additional detail.

First, targeted disruption of a SASPase gene is described, in the order of cloning of a SASPase gene, construction of a targeting vector used for targeted disruption, and acquisition of ES cells that have undergone homologous recombination.

1. Cloning of a DNA Containing a Portion of SASPase Gene

A DNA encoding SASPase can be obtained by preparing primers based on the nucleotide sequence of SEQ ID NO: 1, and by performing PCR with genomic DNAs or cDNAs of a non-human animal or by performing RT-PCR with RNAs of a non-human animal. Alternatively, a probe can be synthesized based on the nucleotide sequence described in the above-mentioned literature (Bernard D. et al.), a genomic DNA library or cDNA library of a non-human animal can be screened for clones that hybridize with the probe, and their nucleotide sequences can be determined to select clones that contain a SASPase gene or a portion thereof, preferably a nucleotide sequence of 500 bp or more, and more preferably a nucleotide sequence of 1 kbp or more.

A restriction map is then generated by confirming restriction enzyme cleavage sites contained in the cloned DNAs. When a DNA clone of a sufficient length for homologous recombination, preferably of 7 kbp or more, and more preferably of 10 kbp or more, is not obtained, DNAs may be excised from multiple clones at suitable restriction sites and then ligated together.

The present invention also relates to uses of DNAs encoding SASPase or portions thereof, preferably DNAs containing the nucleotide sequence of 500 bp or more, more preferably 1 kbp or more, even more preferably 2 kbp or more, and even more preferably 3 kbp or more of the DNAs encoding SASPase, for producing SASPase KO animals, animals having wrinkles, or animal models of wrinkles.

2. Construction of a Targeting Vector

A positive selection marker such as a drug resistance gene, more preferably a neomycin resistance gene, is introduced into a restriction site in the exon region of the resulting DNA of sufficient length for recombination. Alternatively, a portion of the exon may be removed and replaced with a drug resistance gene. In the absence of a suitable restriction site, it may be introduced by, for example, using PCR or ligating an oligonucleotide containing a restriction site.

Preferably, the vector contains a negative selection marker, such as the thymidine kinase gene or diphtheria toxin gene, to remove embryonic stem cells (ES cells) in which homologous recombination has not occurred between the introduced DNA and the SASPase gene and the introduced DNA has been inserted into a site other than the SASPase gene.

Examples of such DNA recombination methods for engineering nucleotide sequences of DNAs include, for example, methods described in Sambruck, J., Fritsch, E. F., and Maniatis, T. (1989), Molecular Cloning: A Laboratory Manual, Cold Spring Harbor Laboratory, Cold Spring Harbor, N.Y.; however, the present invention is not limited thereto and encompasses any method that as allows one to obtain a suitable recombinant DNA.

The present invention relates to targeting vectors used to disrupt a gene encoding SASPase. The targeting vectors contain a portion of a DNA encoding SASPase, preferably a nucleotide sequence of 500 bp or more, more preferably 1 kbp or more, even more preferably 2 kbp or more, and even more preferably 3 kbp or more of a DNA encoding SASPase, and contain a DNA in which the genetic sequence has been altered by deletion, addition, substitution or the like so as to prevent expression of functional SASPase. Preferably, the targeting vectors for a gene encoding SASPase contain an exogenous nucleic acid, preferably a desired marker gene, and preferably a drug resistance gene, in a portion of a DNA encoding SASPase, preferably a nucleotide sequence of 500 bp or more, more preferably 1 kbp or more, even more preferably 2 kbp or more, and even more preferably 3 kbp or more of a DNA encoding SASPase. More preferably, the targeting vectors contain a negative marker, such as the thymidine kinase gene or diphtheria toxin gene. The present invention also relates to uses of the targeting vectors to produce SASPase KO animals, animals having wrinkles, or animal models of wrinkles.

3. Acquisition of ES Cells that have Undergone Homologous Recombination

The prepared targeting vector is cleaved with a restriction enzyme to obtain a linear DNA, purified by, for example, phenol-chloroform extraction, agarose gel electrophoresis, or ultracentrifugation, and then transfected into ES cells such as TT2 cells (Yagi T. et al., Anal. Biochem., 214: 70-76, 1993). In the present invention, transfection methods include, but are not limited to, electroporation and lipofection. Examples of suitable ES cells include animal ES cells such as those derived from rats (Iannaccone, P M et al., Dev. Biol. 163: 288-292, 1994), monkeys (Thomson J A, et al: Proc Natl Acad Sci USA (1995) 92: 7844-7848), rabbits (Schoonjans L et al., Mol. Reprod. Dev. 1996; 45: 439-443), minks (Sukoyan, M. A. et al. (1993) Mol. Reprod. Dev. 36, 148-158), hamsters (Doetschman T et al., Dev Biol 1988; 127: 224-227), pigs (Wheeler, M. B. (1994) Reprod. Fertil. Dev. 6, 563-568; Shim, H., et al. (1997) Biol. Reprod. 57, 1089-1095), and marmosets (Thomson, J. A. et al. (1996) Biol. Reprod. 55, 254-259; Thomson J A et al., Curr Top Dev Biol (1998) 38: 133-165).

The transfected cells are cultured in any suitable selective medium. For example, when a targeting vector is constructed to incorporate the neomycin resistance gene and thymidine kinase gene, cells are cultured in a selective medium containing neomycin and ganciclovir.

Incorporation of an introduced gene, such as the neomycin resistance gene, into the ES cells that show resistance to both drugs and proliferate can be easily confirmed by PCR and the like. Moreover, whether or not homologous recombination has occurred can be confirmed by Southern blot analysis, using as a probe a portion of the DNA of the 5' side upstream or the 3' side downstream outside the targeting vector. In addition, Southern blot analysis can be used to confirm that the targeting vector has not been randomly inserted, for example, using as a probe a DNA within the targeting vector. ES cells that have undergone homologous recombination can be acquired by combining these methods.

Next, a method for producing a knockout mouse is described; however, the present invention is not limited to the described method.

Knockout mice are produced through the following steps: collecting 8-cell stage embryos or blastocysts after fertilization; microinjecting with ES cells that have undergone homologous recombination; transplanting the manipulated eggs into pseudopregnant mice; allowing the pseudopregnant mice to deliver and raising the offspring; selecting transgenic mice by PCR and Southern blotting; and establishing a mouse strain having the transgene (Yagi T. et al., Analytical Biochem. 214, 70, 1993).

1. Collection of 8-Cell Stage Embryos or Blastocysts

5 IU of pregnant mare serum gonadotropin and 2.5 IU of human chorionic gonadotropin are respectively administered intraperitoneally to female mice to induce superovulation, and then 8-cell stage embryos are obtained by tubouterine reflux from the female mice on day 2.5 after fertilization. Furthermore, when using blastocysts, the uterus of the female mice is excised on day 3.5 after fertilization and the blastocysts are obtained by uterine reflux.

2. Microinjection of ES Cells that have Undergone Homologous Recombination

ES cells that have undergone homologous recombination are microinjected into the obtained 8-cell stage embryos or blastocysts. Microinjection can be carried out using a micromanipulator, microinjector, injection pipette, or holding pipette under an inverted microscope, for example, based on the description of Hogan, B. L. M., A Laboratory Manual, Cold Spring Harbor Laboratory Press, Cold Spring Harbor, N.Y., 1986; Yagi T. et al., Analytical Biochem. 214, 70, 1993. In addition, a 5 µl drop of medium and a drop of a suspension of ES cells are placed in a dish such as Falcon 3002 (Becton Dickinson Labware) and liquid paraffin is layered on them to prepare an injection dish. Herein below, the 8-cell stage embryos or blastocysts microinjected with ES cells that have undergone homologous recombination are referred to as manipulated eggs.

3. Transplantation of Manipulated Eggs into Pseudopregnant Mice

Normal female mice are crossed with vasoligated male mice to produce pseudopregnant female mice, and then transplanted with the manipulated eggs. Transplantation of the manipulated eggs can be carried out, for example, according to Hogan, B. L. M., A Laboratory Manual, Cold Spring Harbor Laboratory Press, Cold Spring Harbor, N.Y., 1986; Yagi T. et al., Analytical Biochem. 214, 70, 1993. Exemplary procedures are described below; however, the present invention is not limited thereto.

The pseudopregnant mice are given general anesthesia using, for example, sodium pentobarbital at 50 mg/kg body weight, after which the ovaries and oviducts are exposed by incising both tendons about 1 cm, and the ovarian bursa is incised with a forceps under a stereoscopic microscope to expose the fimbriae tubae. Next, 7 to 8 of the manipulated eggs are transferred to the fimbriae tubae of each oviduct. At this point, transplantation into the oviduct is confirmed by the presence of microbubbles inserted together with the manipulated eggs. Subsequently, the oviducts and ovaries are returned to the abdominal cavity, the incisions are sutured, and the mice are allowed to awake from the anesthesia. In some cases, the manipulated eggs may be cultured until the following day to develop into blastocysts and then transplanted into the uterus.

4. Delivery of Pseudopregnant Mice and Raising of their Offspring

In many cases, mice offspring are obtained by day 17 after the transplantation. The mice offspring are typically chimeras of homologously recombined ES cells and cells of the mouse from which fertilized eggs were collected. For example, when TT2 cells are used as ES cells and injected into 8-cell stage embryos harvested from an ICR, agouti hair color is dominant in mice offspring having a high chimeric rate, while white hair color is dominant in mice offspring having a low chimeric rate.

5. Selection of Transgenic Mice by PCR and Southern Blotting

Whether or not germ cells contain the transgene can be easily confirmed by the hair color of mouse offspring obtained by crossing with a mouse with white hair, such as an ICR. Alternatively, since germ cells of mice having a high chimeric rate are expected to contain the transgene as well, the presence of the transgene can be confirmed by crossing mice having as high a chimeric rate as possible, extracting DNAs from the tail of the obtained mice offspring, and performing PCR. In addition, genotype can be identified more accurately by performing Southern blot analysis instead of PCR.

The present invention also relates to methods for producing SASPase KO animals, animals having wrinkles, or animal models of wrinkles, such methods including the following steps: (i) introducing a targeting vector for a gene encoding SASPase into ES cells; (ii) selecting ES cells in which recombination has occurred between the gene site encoding SASPase of the ES cells and the targeting vector; and (iii) generating animals from the ES cells. Animals can be generated from the ES cells, for example, by injecting the ES cells into 8-cell stage embryos or blastocysts and then transplanting into the oviduct of pseudopregnant females. The resulting chimeric KO animals can be further crossed to obtain hetero KO animals, in which one of the alleles encoding SASPase is disrupted in all cells, and homo KO animals, in which both alleles are disrupted. Hetero KO animals are useful for producing homo KO animals.

A gene knockout animal can also be produced using somatic cell cloning techniques, without using ES cells. For example, gene targeting in sheep using nuclear transplantation can be carried out according to McCreath, K J. et al., Nature 2000, 405: 1066-1069, and gene targeting in pigs can be carried out according to Lai L, et al., Science 2002, 295: 1089-1092; Dai Y. et al., Nat. Biotechnol. 2002, 20: 251-255; Ramsoondar J J. et al., Biol Reprod 2003, 2: 2; Phelps C J. et al., Science 2003, 299: 411-414. In addition, gene targeting in cows can be carried out according to Kuroiwa, Y. et al, Nat. Genet. 36, 775-780 (2004).

SASPase KO animals have more wrinkles and/or sags on the sides of the body and such as compared with wild-type animals. Such wrinkles and sags are postulated to arise as a result of the abnormality in metabolism of the stratum corneum that has been caused by deficiency of SASPase at the granular layer of the epidermis. Thus, the SASPase animals of the present invention find utility as animal models of metabolic diseases of the stratum corneum.

6. Establishment of a Mouse Strain Having a Transgene

Hetero mice (hereinafter referred to as He mice) can be crossed each other to obtain SASPase KO mice in which the transgene is present homozygously in the obtained mice offspring. SASPase KO mice can also be obtained by crossing between He mice, an He mouse and a SASPase KO mouse, and SASPase KO mice.

The presence or absence of mRNA expression of SASPase KO mice can be confirmed by, for example, Northern blot analysis, RT-PCR, RNase protection assay or in situ. In addition, expression of the SASPase protein can be confirmed by immunohistochemical staining. Furthermore, the absence of SASPase at the granular layer of the epidermis can be confirmed by immunostaining and the like.

The present invention further relates to uses of non-human animals deficient in SASPase (SASPase KO animals).

SASPase KO animals can be used to analyze SASPase functions. Functions of SASPase in wild-type animals can be analyzed based on phenotypes of the SASPase KO animals by comparing the SASPase KO animals with the wild-type animal.

SASPase KO animals can also be used to analyze the functions of SASPase in ontogenesis based on their phenotypes.

As a clear example of such functions, it was discovered herein that SASPase plays an important role in skin morphogenesis. This was achieved starting from the finding that SASPase KO mice demonstrated a large number of wrinkles on the sides of the body. Since these wrinkles were observed more prominently in females than in males, it was suggested that gender differences in skin have an effect on wrinkle formation.

Thus, it is indicated that unique functions of SASPase can be analyzed by comparing and observing the phenotypes of SASPase KO mice and wild-type mice. For example, the present invention relates to methods for detecting wrinkles and/or sags, such methods including the step of detecting wrinkles and/or sags in animals in which a gene encoding SASPase or a gene homologous to the gene has been deleted. In addition, the present invention relates to animals for detecting wrinkles and/or sags in which a gene encoding SASPase or a gene homologous to the gene has been deleted. The present invention also relates to uses of animals in which a gene encoding SASPase or a gene homologous to the gene has been deleted, for detecting wrinkles and/or sags.

Furthermore, the present invention discloses uses of SASPase KO animals as animal models of diseases caused by a deficiency of SASPase. Since SASPase KO animals are deficient in SASPase, they can be used as animal models of wrinkles to analyze wrinkles and develop treatment methods or therapeutic agents. For example, SASPase KO animals of the present invention may be used as animal models of wrinkles to investigate effects of test compounds on wrinkles. A specific example of this method includes the following steps: (i) administering a test compound to a SASPase KO animal; (ii) measuring wrinkles on the animal; and (iii) identifying differences in wrinkles as compared to when the test compound is not administered. In addition, SASPase KO animals of the present invention can be used as animal models of wrinkles to investigate effects of desired treatments which may be effective to prevent or reduce wrinkles. A specific example of this method includes the following steps: (i) performing a desired treatment on a SASPase KO animal; (ii) measuring wrinkles on the animal; and (iii) identifying differences in wrinkles as compared to when the treatment is not performed. Wrinkles can be measured by using as an indicator an arbitrary measurement of wrinkles, such as the time of appearance of wrinkles and the form of wrinkles, and preferably determining the degree of wrinkles, such as the number, density, and depth of wrinkles.

The uses of SASPase KO animals for analyzing functions of SASPase in wrinkle formation and the uses of SASPase KO animals as animal models of wrinkles as herein shown are illustrative of the present invention, and the present invention is not limited thereto.

EFFECT OF THE INVENTION

The present invention discloses methods for producing SASPase KO animals in which SASPase is not functionally expressed, and characteristics thereof. The present invention enables the use of SASPase KO animals as animal models of wrinkles caused by a deficiency of SASPase, as well as analysis of unique functions of SASPase. For example, wrinkles and/or sags in SASPase KO animals can be used as indicators to assay or screen for pharmaceutical agents and treatment methods for reducing wrinkles and/or sags. In addition, by producing a disease condition in a SASPase KO animal, it can be examined to what extent SASPase is involved in the formation of the disease condition and the effectiveness of a SASPase inhibitor can be confirmed. Moreover, when recombinant SASPase is used as a cosmetic or therapeutic agent, its activity can be confirmed using wrinkles of a SASPase KO animal as an indicator.

EXAMPLES

Herein below, the present invention is specifically described with reference to Examples; however, it should not to be construed as being limited thereto. Furthermore, references cited herein are incorporated by reference herein, as if a part of the present description.

Example 1

Cloning of a SASPase Gene

Public genome databases were searched based on the nucleotide sequence of the mouse SASPase gene described in SEQ ID NO: 1 to design primers for amplifying the 5' side 2.2 Kb and 3' side 7.7 Kb genomic regions of the mouse SASPase gene. These primers were then used to isolate the 5' side and 3' side genomic regions of the SASPase gene from the 129SVJ mouse genome by genomic PCR.

Example 2

Construction of a Targeting Vector

A targeting vector was produced in which the neomycin resistance gene containing a promoter was located between the 5' side and 3' side homologous regions relative to the exon of the SASPase gene.

Genomic DNA clones containing the 5' side homologous region were subjected to blunting. Genomic DNA clones containing the 3' side homologous region were cleaved at the SalI and ApaI sites, which were present within the PCR primer. A blunting site and SalI and ApaI cleavage sites were respectively produced in turn on both sides of the neomycin resistance gene in pBluescript™ SK(-) into which the gene had been inserted, and the 5' side and 3' side homologous regions were introduced into the resulting vector to ultimately produce the targeting vector (FIG. 1).

Example 3

Acquisition of ES Cells that have Undergone Homologous Recombination

The targeting vector was cleaved with NotI to obtain a linear DNA (1 mg/ml). Electroporation into ES cells was carried out by Kurabo Industries, Ltd. DNAs were extracted from a portion of the resulting ES cell colonies, and clones that had undergone homologous recombination were identified by Southern blot analysis. Southern blot analysis was carried out by using as a probe a genomic DNA of the 5' side of the portion that is not contained in the targeting vector, and then a 2.7 Kb DNA fragment was detected in clones with homologous recombination relative to a 6.8 Kb in the wild type.

Example 4

Production of SASPase KO Mice

The ES cells that have undergone homologous recombination were injected into female mice by Kurabo Industries, Ltd. Hetero (He) mice were obtained by crossing the resulting chimeric mice with C57BL/6 mice, and then knockout (KO) mice were obtained by crossing between He mice.

The genotypes of the resulting mice were confirmed by the size of the DNA fragment produced by PCR. A 2 to 3 mm portion of the mouse tail was cut off and digested (overnight at 55° C.) with Proteinase K (0.25 mg/ml). Next, the genomic DNA was extracted in accordance with a conventional method and dissolved in 100 µl to 200 µl of distilled water to prepare a PCR template. When primers were designed for the sequence contained in the neomycin gene (P3: SEQ ID NO: 3) and for two sites in the SASPase gene (P1 and P2: SEQ ID NO: 4 and SEQ ID NO: 5), and then PCR was performed. As a result, a PCR product of 460 bp (product obtained from SEQ ID NO: 3 and SEQ ID NO: 4) was obtained from a mutated gene, while a PCR product of 670 bp (product obtained from SEQ ID NO: 4 and SEQ ID NO: 5) was obtained from the wild-type gene, and the genotype of each individual was identified based on the PCR product.

The genotypes were also confirmed by Southern blot analysis. Genomic DNAs extracted from the mouse tails were cleaved by EcoRI, and it was confirmed that a 2.7 kb signal was detected in the KO mice.

Expression of SASPase in the SASPase KO mice was confirmed by Western blotting. Proteins were extracted from the skin of three mice of each genotype using a solution containing 3% sodium dodecyl sulfate and 1% mercaptoethanol. The proteins were electrophoresed on a 15% acrylamide gel and the deficiency of SASPase was confirmed using an anti-SASPase antibody. Immunohistological test using mouse skin frozen sections also showed a complete deficiency of SASPase.

Figure 2:
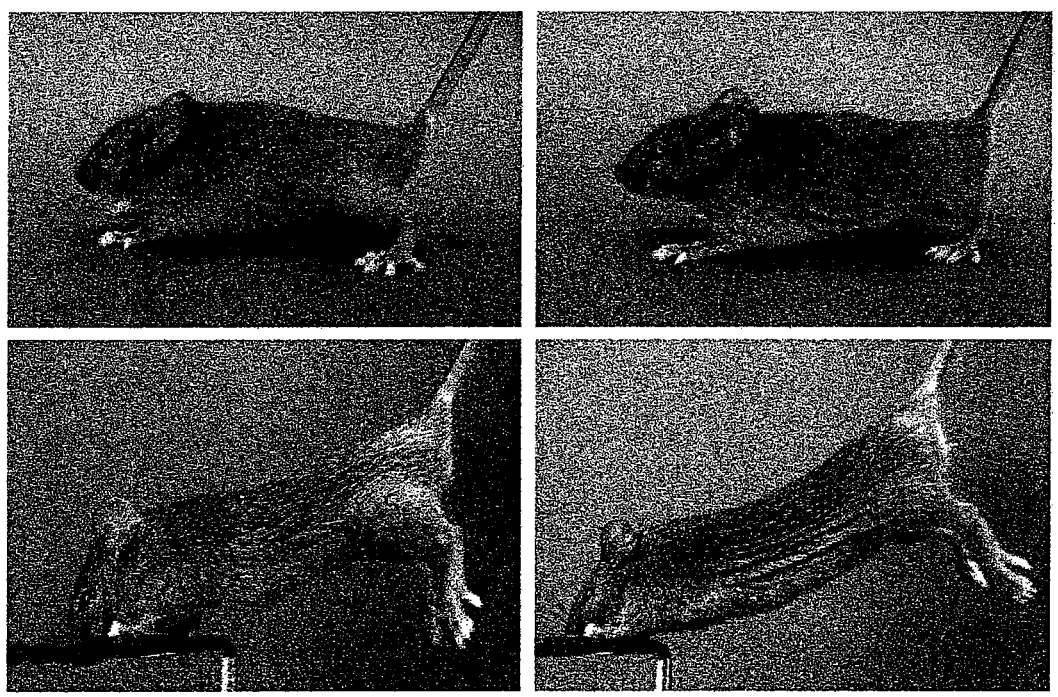
FIG. 2 is composed of a series of photographs depicting the appearance of a SASPase KO mouse. Part A depicts the sagging skin observed on the side of the body in a SASPase KO mouse (upper right) among 9-week-old female mice in resting state. Wrinkles in the SASPase KO mouse became more prominent when the forelimbs were immobilized and extended to the rear (lower right). Part B depicts the appearance of mice after the back was shaved. Wrinkles were prominently observed in the SASPase KO mouse (–/–).
Figure 2:
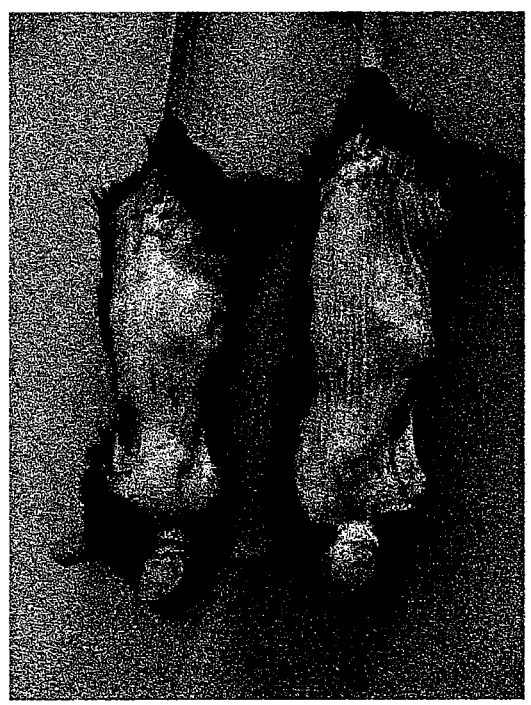

The SASPase KO mice were observed to have numerous wrinkles parallel to the sides of the body, starting from the age of about 5 weeks, and suggested to be useful as a model for analyzing wrinkles attributable to the epidermis (FIG. 2).

Example 5

Differences Between SASPase KO Mice and Normal Mice

Figure 3:
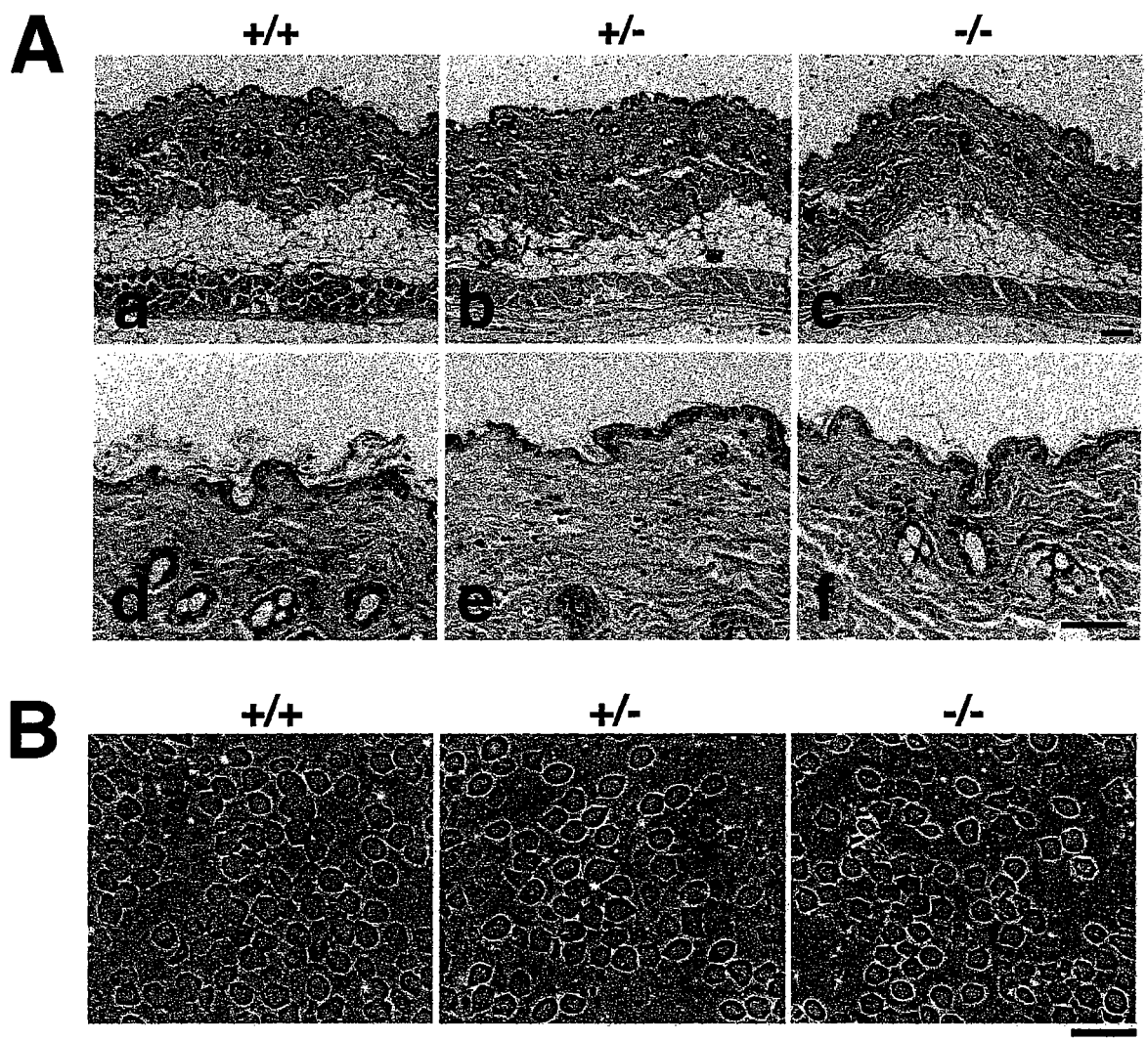
FIG. 3 depicts the results of histochemical analysis of SASPase KO mice. Part A is composed of hematoxylin-eosin stained images of 14-week-old SASPase +/+ mice (+/+; a and d), SASPase +/– mice (+/–; b and e), and SASPase –/– mice (–/–; c and f). Scale bar: 50 µm. Part B depicts corneocytes of a SASPase –/– mouse. Corneocytes were isolated by boiling the ears of a 14-week-old mouse in the presence of SDS and dithiothreitol (DTT). Scale bar: 50 µm.

When a histochemical analysis was performed to further analyze the wrinkles of SASPase KO mice, all cell layers were confirmed to be formed normally (FIG. 3A). In addition, other stratified squamous epithelia such as the hair, ears, esophagus, forestomach, and urinary bladder were also normal.

Next, corneocytes were isolated from the ears and analyzed. The mouse ear was excised, placed in pure water containing 25 mM DTT and 2% SDS, and boiled for 15 minutes. The mixture was subsequently centrifuged and the precipitate was resuspended in a solution of 10 mM Tris-Cl (pH 8.0) and 1 mM EDTA followed by observation in a hemocytometer. No differences were observed between the SASPase KO mice and normal mice (FIG. 3B).

Next, the expression status of several epidermal differentiation markers was analyzed to determine the differentiation status of the epidermis in SASPase KO mice.

Figure 4:
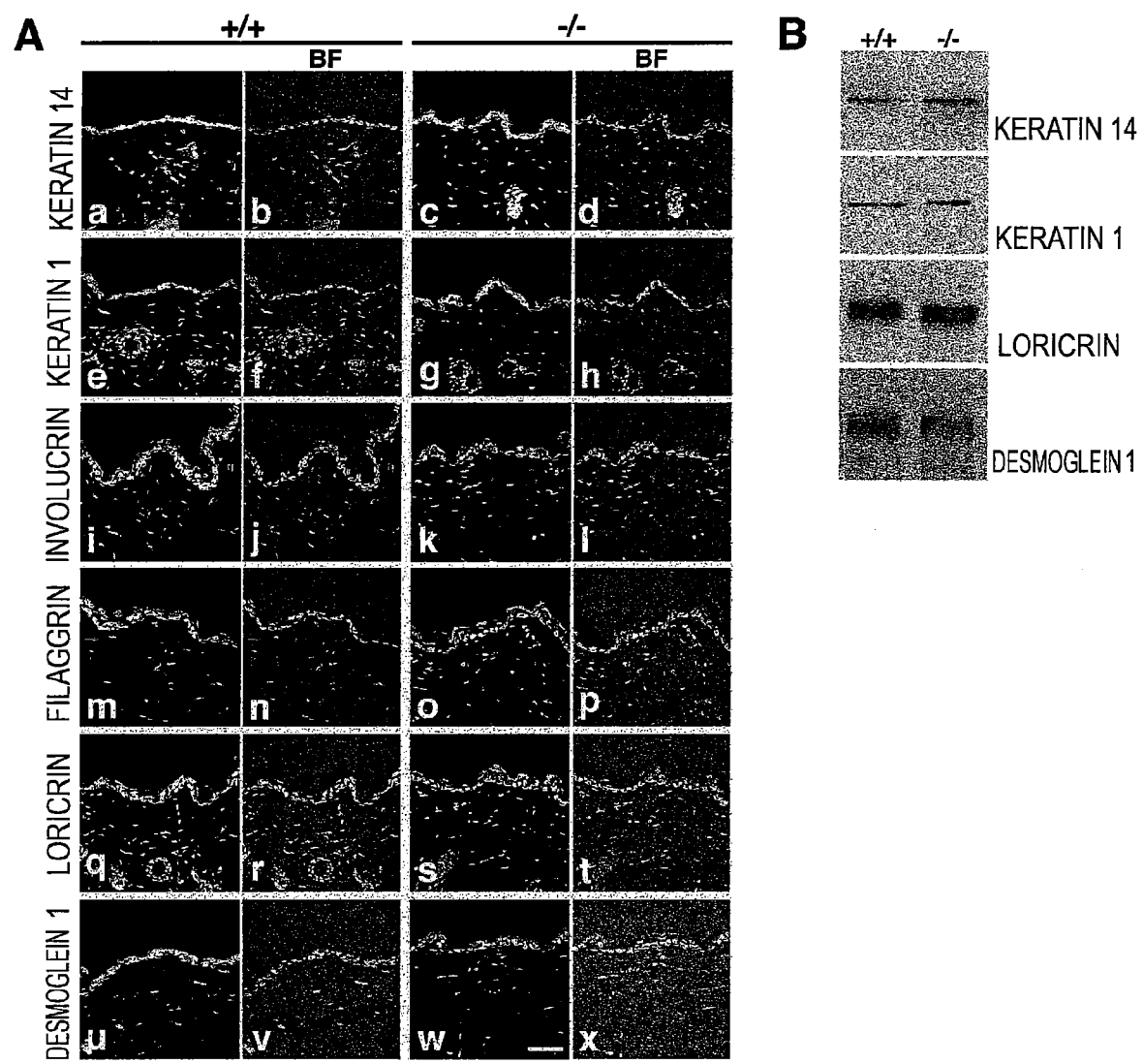
FIG. 4 presents the normal expression of epidermal differentiation markers in SASPase KO mice. Part A is composed of confocal microscopic images (1st and 3rd columns) of 9-week-old SASPase +/+ mice (+/+; a, b, e, f, i, j, m, n, q, r, u, and v) and SASPase –/– mice (–/–; c, d, g, h, k, l, o, p, s, t, w, and x) stained with an anti-keratin 14 antibody (a and c), anti-keratin 1 antibody (e and g), anti-involucrin antibody (i and k), anti-filaggrin antibody (m and o), anti-loricrin antibody (q and s), and anti-desmoglein 1 antibody (u and w). Nuclei were stained with SYTOX green. The epidermal differentiation markers are normal distributed in mSASP –/– mice. The dotted lines indicate the boundary between the epidermis and dermis. BF: bright field images (2nd and 4th columns). Scale bar: 50 µm. Part B depicts the results of immunoblot analysis of epidermal extracts (10 µg) from a 9-week-old SASPase +/+ mouse and SASPase –/– mouse using an anti-keratin 14, anti-keratin 1, anti-loricrin, and anti-desmoglein 1 antibodies.

Skin from the side of the mice was fixed in 2% paraformaldehyde/PBS at room temperature for 1 hour and then treated in 10% sucrose/PBS and 20% sucrose/PBS for 3 hours and O/N at 4° C., respectively. The skin was subsequently embedded in Tissue-TEK O.C.T. Compound (Sakura Finetechnical) and frozen with dry ice. Next, sections with a thickness of 10 μm were prepared, dried on silane-coated slide glasses, and then treated in Block-Ace blocking solution (Dainippon Pharmaceutical) for 1 hour at room temperature. A primary antibody was then added and left to stand for 1 hour at room temperature. After washing three times with PBS, the sections were treated in a mixture of Alexa 488-goat anti-rabbit IgG (Molecular Probes) and SYTOX Green (Molecular Probes) for 30 minutes at room temperature. Next, the sections were washed three times with PBS and then mounted in 50% glycerol/PBS. LSM510 confocal laser scanning microscope (version 23.3; Carl Zeiss Inc.) was used as a confocal microscope. As shown in FIG. 4A, there were no differences between the SASPase KO mice and normal mice in the expression level and localization of keratin 14, keratin 1, involucrin, filaggrin, loricrin, and desmoglein 1 that was shown by immunostaining for these markers in the epidermis.

In addition, SASPase KO mice and normal mice were compared by performing immunoblotting for keratin 14, keratin 1, and desmoglein 1 in their epidermal extracts. The epidermis and dermis were isolated by heating mouse skin in 5 mM EDTA/PBS for 5 minutes at 54° C., and the epidermis was placed in 62.5 mM Tris-Cl (pH 6.8), 2% glycerol, 1% SDS, 5 mM EDTA, and protease inhibitor cocktail (Nakalai Tesque) and subjected to ultrasonic treatment (3 seconds, 5 times) to extract proteins. Next, the proteins were centrifuged for 20 minutes at room temperature at 15,000×g and the obtained supernatant was used as an epidermal extract. This epidermal extract was subjected to SDS-PAGE on a 15% acrylamide gel, transferred onto a nitrocellulose membrane, and then incubated with a primary antibody. The bound antibody was visualized with a secondary antibody conjugated with alkaline phosphatase. There were also no differences between the SASPase KO mice and normal mice in the results of immunoblotting for keratin 14, keratin 1, and desmoglein 1 in the epidermal extracts (FIG. 4B).

INDUSTRIAL APPLICABILITY

The present invention provides SASPase KO animals in which a gene encoding SASPase has been disrupted and the expression of functional SASPase is suppressed. The SASPase KO animals find utility as animal models of wrinkles, and the skin, cells, and other tissues and cells of such animals are expected to be used as models of wrinkles and other metabolic abnormalities in skin.

The invention claimed is:

1. A knockout mouse whose genome comprises a homozygous disruption in a stratified epithelium-specific protease (SASPase) gene, wherein the mouse has increased wrinkles as compared to a mouse whose genome comprises a heterozygous disruption in the SASPase gene.

2. The mouse of claim 1, wherein the SASPase gene encodes the cDNA of SEQ ID NO: 1.

3. A method of identifying a test compound that reduces wrinkles, the method comprising: a) administering the test compound to the mouse of claim 1, b) measuring a wrinkle in the mouse, and c) identifying a test compound that reduces wrinkles in the mouse.

* * * * *